US008962892B2

(12) United States Patent
Ignatyev et al.

(10) Patent No.: US 8,962,892 B2
(45) Date of Patent: Feb. 24, 2015

(54) PROCESS FOR THE PREPARATION OF TRIS(PERFLUOROALKYL)PHOSPHINE OXIDES

(75) Inventors: Nikolai Mykola Ignatyev, Duisburg (DE); Waldemar Wiebe, Cologne (DE); Helge Willner, Muelheim/Ruhr (DE)

(73) Assignee: MERCK PATENT GmbH, Darmstadt (DE)

( * ) Notice: Subject to any disclaimer, the term of this patent is extended or adjusted under 35 U.S.C. 154(b) by 221 days.

(21) Appl. No.: 13/583,665

(22) PCT Filed: Feb. 17, 2011

(86) PCT No.: PCT/EP2011/000765
§ 371 (c)(1),
(2), (4) Date: Sep. 10, 2012

(87) PCT Pub. No.: WO2011/110281
PCT Pub. Date: Sep. 15, 2011

(65) Prior Publication Data
US 2012/0330063 A1 Dec. 27, 2012

(30) Foreign Application Priority Data
Mar. 11, 2010 (DE) .......................... 10 2010 011 034

(51) Int. Cl.
C07F 9/02 (2006.01)
C07F 9/535 (2006.01)
C07F 9/53 (2006.01)

(52) U.S. Cl.
CPC ............... *C07F 9/535* (2013.01); *C07F 9/5304* (2013.01)
USPC .......................................................... 568/16

(58) Field of Classification Search
None
See application file for complete search history.

(56) References Cited

U.S. PATENT DOCUMENTS 6,264,818 B1 7/2001 Heider et al.
2005/0119513 A1 6/2005 Ignatyev et al.

FOREIGN PATENT DOCUMENTS

EP 1 037 896 B1 9/2000
WO 00/21969 A1 4/2000
WO 03/087020 A1 10/2003

OTHER PUBLICATIONS

Mahmood, T. et al., "New Perfluoroalkylphosphonic and Bis(perfluoroalkyl)phosphinic Acids and Their Precursors," Inorganic Chemistry, 1986, vol. 25, pp. 3128-3131.
Paul, R. C., "The Preparation of Tristrifluoromethylphosphine Oxide," Journal of the Chemical Society, 1955, pp. 574-575.
Semenii, V. Ya. et al, "Difluorotis(Perfluoralkyl)Phosphoranes," Zh. Obshch. Khim, Jan. 19, 2007, vol. 55, No. 12, pp. 2716-2720, XP-002246309; Cited in International Search Report, dated May 25, 2011, issued in the corresponding PCT/EP2011/000765.
Ignat'Ev, N., et al., "Electrochemical fluorination of trialkylphosphines," Journal of Fluorine Chemistry, 2000, vol. 103, pp. 57-61, Elsevier Science S.A.
Bennett, F.W., et al., "Organometallic and Organometalloidal Fluorine Compounds. Part VII. Trifluoromethyl Compounds of Phosphorus," Journal of the Chemical Society, 1953, pp. 1565-1571.
Gorg, M., et al., "Facile syntheses of tris(trifluoromethyl)phosphine and difluorotris(trifluoromethyl) phosphorane," Journal of Fluorine Chemistry, 1996, vol. 79, pp. 103-104.
International Search Report, dated May 25, 2011, issued in the corresponding PCT/EP2011/000765.

*Primary Examiner* — Clinton Brooks
(74) *Attorney, Agent, or Firm* — Millen, White, Zelano & Branigan, P.C.

(57) ABSTRACT

The invention relates to a process for the preparation of tris (perfluoroalkyl)phosphine oxides by reaction of tris(perfluoroalkyl)difluorophosphorane with alkaline-earth metal oxides, alkaline-earth metal carbonates, zinc oxide, copper(I) oxide, copper(II) oxide, silver oxide, mercury(II) oxide, cadmium oxide or cadmium carbonate.

18 Claims, No Drawings

PROCESS FOR THE PREPARATION OF TRIS(PERFLUOROALKYL)PHOSPHINE OXIDES

The invention relates to a process for the preparation of tris(perfluoroalkyl)phosphine oxides by reaction of tris(perfluoroalkyl)difluorophosphorane with alkaline-earth metal oxides, alkaline-earth metal carbonates, zinc oxide, copper(I) oxide, copper(II) oxide, silver oxide, mercury(II) oxide, cadmium oxide or cadmium carbonate.

Tris(perfluoroalkyl)phosphine oxides are known perfluoroalkylating agents or interesting starting materials for a multiplicity of interesting compounds, for example for the synthesis of bis(perfluoroalkyl)phosphinic acids, bis(perfluoroalkyl)phosphinates, perfluoroalkylborates or perfluorinated alcohols, such as, for example, $(C_6H_5)_2C(OH)C_2F_5$.

R. C. Paul, J. Chem. Soc., 1955, 574-575 describes, for example, the synthesis of tris(trifluoromethyl)phosphine oxide by heating tris(trifluoromethyl)dichlorophosphorane $[(CF_3)_3PCl_2]$ with an excess of anhydrous oxalic acid. The disadvantage of this synthesis is the relatively difficult access to tris(trifluoromethyl)dichlorophosphorane.

V. Ya. Semenii et al, Zh. Obshch. Khim, 55, 12, 1985, 2716-2720 describes the synthesis of tris(perfluoroalkyl)phosphine oxides by reaction of difluorotris(perfluoroalkyl)phosphoranes with hexamethyldisiloxane ($[(CH_3)_3Si]_2O$). The disadvantage of this synthesis is the expensive starting material hexamethyldisiloxane and the formation of the highly flammable by-product trimethylsilyl fluoride in twice the molar amount. A complicating factor in the synthesis of tris(pentafluoroethyl)phosphine oxide is that this product has a boiling point of 101° C. and the starting material hexamethyldisiloxane has a boiling point of 99-100° C. Distillative separation of even small amounts of starting material is therefore made more difficult.

It is therefore desirable to have available an economical synthesis of the phosphine oxides described which can be implemented on a large industrial scale in order that this interesting class of starting materials or perfluoroalkylating agents can be prepared in large amounts.

The object of the invention is therefore to develop an improved process for the preparation of tris(perfluoroalkyl)phosphine oxides which meets the requirements of an economical large-scale industrial synthesis and which does not have the disadvantages of the prior art.

This object is achieved in accordance with the invention by the features of the main claim and the subordinate claims.

Surprisingly, it has been found that the tris(perfluoroalkyl)difluorophosphoranes known as starting materials are capable of reacting with alkaline-earth metal oxides, alkaline-earth metal carbonates, zinc oxide, copper(I) oxide, copper(II) oxide, silver oxide, mercury(II) oxide, cadmium oxide or cadmium carbonate, which are employed as solids, and achieving the desired phosphine oxides. The by-products formed are alkaline-earth metal fluorides, which, in the case of calcium difluoride, even correspond to a naturally occurring compound.

The invention therefore relates to a process for the preparation of compounds of the formula (I)

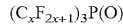     (I), where x is 1, 2, 3, 4, 5, 6, 7, 8, 9, 10, 11 or 12, by reaction of compounds of the formula (II)

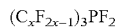     (II), where x has one of the meanings indicated above, with alkaline-earth metal oxides, alkaline-earth metal carbonates, zinc oxide, copper(I) oxide, copper(II) oxide, silver oxide, mercury(II) oxide, cadmium oxide or cadmium carbonate.

Preference is given to the preparation in accordance with the invention of compounds of the formula (I) in which x corresponds to 2, 3, 4, 5 or 6. Accordingly, starting materials of the formula (II) in which x denotes 2, 3, 4, 5 or 6 are preferred.

The invention therefore also relates to the process, as described above, characterised in that compounds of the formula (II) in which x denotes 2, 3, 4, 5 or 6 are employed.

Particular preference is given to the preparation in accordance with the invention of compounds of the formula (I) in which x denotes 2, 4 or 6, very particularly preferably the preparation of tris(pentafluoroethyl)phosphine oxide or tris(nonafluorobutyl)phosphine oxide.

By-products formed alongside the compounds of the formula (I), as described above, are the metal fluorides of the alkaline-earth metals, zinc, copper, silver, mercury or cadmium. The process according to the invention can therefore also be thought of as a process for the preparation of metal fluorides of the alkaline-earth metals, zinc, copper, silver, mercury or cadmium. In particular, this process according to the invention enables the preparation of anhydrous metal fluorides, so long as anhydrous metal oxides or metal carbonates are used in the reaction.

The compounds of the formula (II) are commercially available or can be prepared by known processes which are familiar to the person skilled in the art.

The preparation of the compounds of the formula (II) can be prepared, for example, by electrochemical fluorination of suitable starting compounds, as described in V. Ya. Semenii et al, Zh. Obshch. Khim., 55, 12, 1985, 2716-2720, N. Ignatiev et al, J. of Fluorine Chem., 103, 2000, 57-61 and WO 00/21969. The corresponding descriptions are hereby incorporated as reference and are regarded as part of the disclosure.

Perfluoroalkylfluorophosphoranes can also be prepared, for example, starting from elemental phosphorus and perfluoroalkyl iodides, based on the description by F. W. Bennett et al, J. Chem. Soc., 1953, 1565-1571 and M. Görg et al, J. Fluorine Chem., 1996, 79, 103-104.

Preferred compounds of the formula (II) are selected from tris(pentafluoroethyl)difluorophosphorane, tris(heptafluoropropyl)difluorophosphorane, tris(nonafluorobutyl)difluorophosphorane, tris(undecafluoropentyl)difluorophosphorane, tris(tridecafluorohexyl)difluorophosphorane.

In principle, all alkaline-earth metal oxides or alkaline-earth metal carbonates can be employed in the process according to the invention. As is known, alkaline-earth metals are magnesium, calcium, strontium and barium. Commercially interesting alkaline-earth metal oxides or alkaline-earth metal carbonates are, for example, calcium oxide (CaO), calcium carbonate ($CaCO_3$), magnesium oxide (MgO) or barium carbonate ($BaCO_3$). The said metal oxides or metal carbonates, as described above, can be used in equimolar amount or an up to two-fold excess. If metal fluorides are prepared as target products, the perfluoroalkylphosphoranes of the formula (II) are preferably used in an excess up to a maximum of 10 mol % relative to the corresponding metal oxides or metal carbonates.

For the synthesis of the compounds of the formula (I), as described above, preference is given to an embodiment of the invention in which alkaline-earth metal oxides or alkaline-earth metal carbonates are employed. The invention therefore relates to a process, as described above, characterised in that alkaline-earth metal oxides or alkaline-earth metal carbonates are used. These are preferably selected from CaO, $CaCO_3$, MgO or $BaCO_3$.

Calcium oxide is very particularly preferably used.

The solids employed in the process according to the invention should preferably be employed in the ground state in order that the greatest possible surface area is present for the reaction.

Any type of grinding is possible, for example grinding by means of a ball mill.

Another alternative is the use of metal oxides in the form of fine particles having a diameter of 10 nm to 0.1 mm, which are preferably employed in the process according to the invention in freshly prepared form. The preparation of such highly active metal oxides from corresponding precursor materials is known to the person skilled in the art and can be carried out by methods which are known in the literature. For example, such highly active metal oxides can be prepared by sol-gel processes, in which a suitable precursor compound, for example a corresponding metal acetate, is hydrolysed in alcohol or an alcohol/water mixture.

In the case of the alkaline-earth metal oxides or alkaline-earth metal carbonates, it is preferred to dry the solids in advance. In general, however, a maximum proportion of 10 mol % of water is tolerated in the process according to the invention. In exceptional cases, such as, for example, in the case of the use of copper(I) oxide, the water proportion described even results in an acceleration of the reaction.

The reaction can in principle take place at temperatures between 15° C. and 200° C. If low reaction temperatures are selected, the corresponding reaction time is longer.

The invention therefore also relates to a process, as described above, characterised in that the reaction takes place at temperatures between 15° C. and 200° C.

The reaction is preferably carried out at room temperature if long reaction times in the order of days are desired.

The reaction is preferably carried out at reaction temperatures of 50° C. to 150° C., particularly preferably at reaction temperatures of 70° C. to 130° C. The temperatures indicated in the example part relate here to the reaction temperature of the heating medium used.

The reaction can be carried out in a glass apparatus or in an apparatus made from plastic (such as, for example, Teflon) or steel.

The reaction in the plastic apparatus or in the steel apparatus generally takes longer The reaction is preferably carried out without solvents. However, it is also possible to work in the presence of solvents which are inert to the compounds of the formula (I) and (II), for example dialkyl ethers having alkyl groups of 2 to 4 C atoms, for example diethyl ether, diisopropyl ether, dipropyl ether, dibutyl ether.

The metal fluorides formed are virtually insoluble and can, for example, be separated off easily by filtration or decantation.

However, the compounds of the formula (I) can also be separated off from the metal fluorides formed by condensation or distillation, as described in the example part.

The compounds of the formula (I), as described above, prepared by the process according to the invention are pure compounds and are ideally suitable for the further reaction, in particular for hydrolysis using water for the preparation of bis(perfluoroalkyl)phosphinic acids and/or perfluoroalkylphosphonic acids.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

The NMR spectra were measured at room temperature (20-25° C.) using the BRUKER AVANCE 250 (Examples: 1 and 3) and BRUKER AVANCE 400 (Examples: 2, 4 and 5) spectrometers from Bruker Analytische Messtechnik AG, with a 5 mm $^1$H/BB broad-band probe with deuterium lock, unless indicated otherwise in the examples. The measurement frequencies of the nuclei investigated for AVANCE 250 are: $^1$H: 250.13 MHz; $^{13}$C: 62.90 MHz; $^{19}$F: 235.36 MHz; $^{31}$P: 101.26 MHz. The measurement frequencies of the nuclei investigated for AVANCE 400 are: $^1$H: 400.13 MHz; $^{13}$C: 100.61 MHz; $^{19}$F: 376.50 MHz; $^{31}$P: 162.00 MHz.

The referencing method is indicated separately for each spectrum or for each data set.

Chemicals Used:

| Chemical | Manufacturer | Article Order No. |
|---|---|---|
| CaO, 98% | Sigma-Aldrich | 24856-8 |
| CaO from marble, small pieces, DAB 6 | Merck | 1.02109.1000 |
| MgO for analysis | Merck | 1.05865.0100 |
| $CaCO_3$ precipitated for analysis | Merck | 1.02066.1000 |
| $BaCO_3$ for analysis | Merck | 1.01711.1000 |

Tris(pentafluoroethyl)difluorophosphorane and tris(nonafluorobutyl)difluorophosphorane are prepared as described in WO 00/21969.

Magnesium oxide is dried at 125° C. in vacuo, for example for 20 hours, before use in the reaction according to the invention.

Example 1

Tris(pentafluoroethyl)phosphine oxide, $(C_2F_5)_3P\!\!=\!\!O$

A.

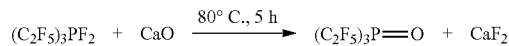

$(C_2F_5)_3PF_2 + CaO \xrightarrow{80°\,C., 5\,h} (C_2F_5)_3P\!\!=\!\!O + CaF_2$ 7.85 g (140 mmol) of finely ground calcium oxide powder (CaO) are initially introduced in a glass apparatus, and 59.6 g (139.9 mmol) of tris(pentafluoroethyl)difluorophosphorane, $(C_2F_5)_3PF_2$, are added at room temperature and with stirring using a magnetic stirrer. The reaction mixture is heated at 80° C. (temperature of the oil bath) with stirring for 5 hours. The product, $(C_2F_5)_3P\!\!=\!\!O$, is subsequently condensed into a cold trap in vacuo, giving 50.3 g of a colourless liquid. The yield of tris(pentafluoroethyl)phosphine oxide corresponds to 89%, calculated from the amount of tris(pentafluoroethyl)difluorophosphorane.

The NMR spectra were measured without solvents for the pure substance. $^{19}$F NMR (pure substance; lock: acetone-$d_6$ film; reference substance: $CCl_3F$), δ, ppm: −82.8 s (9F, $3CF_3$), −120.3 d (6F, $3CF_2$), $^2J_{P,F}$=84 Hz.

$^{31}$P NMR (pure substance; lock: acetone-$d_6$ film; reference substance: 85% $H_3PO_4$), δ, ppm: 19.4 sept, $^2J_{P,F}$=84 Hz.

B.

1.05 g (18.7 mmol) of finely ground calcium oxide powder (CaO) are initially introduced in a glass apparatus, and 1.96 g (4.6 mmol) of tris(pentafluoroethyl)difluorophosphorane, $(C_2F_5)_3PF_2$, are added at room temperature and with stirring using a magnetic stirrer. The reaction mixture is stirred at room temperature for 2 days. The product, $(C_2F_5)_3P=O$, is subsequently condensed into a cold trap in vacuo, giving 1.48 g of a colourless liquid. The yield of tris(pentafluoroethyl)phosphine oxide corresponds to 80%, calculated from the amount of tris(pentafluoroethyl)difluorophosphorane.

The NMR spectra are identical to those of the product from Example 1A.

Example 2

Tris(pentafluoroethyl)phosphine oxide, $(C_2F_5)_3P=O$

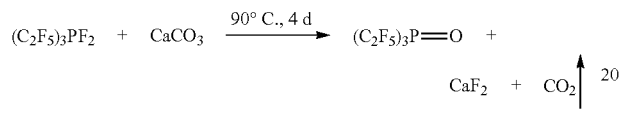

4.97 g (49.7 mmol) of calcium carbonate ($CaCO_3$) are initially introduced in a glass apparatus, and 19.88 g (46.7 mmol) of tris(pentafluoroethyl)difluorophosphorane, $(C_2F_5)_3PF_2$, are added at room temperature and with stirring using a magnetic stirrer. The reaction mixture is heated at 90° C. (temperature of the oil bath) with stirring for 4 days. The product, $(C_2F_5)_3P=O$, is subsequently condensed into a cold trap in vacuo, giving 17.4 g of a colourless liquid. The yield of tris(pentafluoroethyl)phosphine oxide corresponds to 92%, calculated from the amount of tris(pentafluoroethyl)difluorophosphorane.

The NMR spectra are identical to those of the product from Example 1A.

Example 3

Tris(pentafluoroethyl)phosphine oxide, $(C_2F_5)_3P=O$

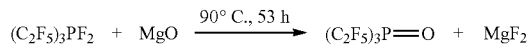

1.89 g (46.9 mmol) of magnesium oxide (MgO, pretreated, as described above) are initially introduced in a glass apparatus, and 20.26 g (47.6 mmol) of tris(pentafluoroethyl)difluorophosphorane, $(C_2F_5)_3PF_2$, are added at room temperature and with stirring using a magnetic stirrer. The reaction mixture is heated at 90° C. (temperature of the oil bath) with stirring for 53 hours. The liquid is subsequently condensed into a cold trap in vacuo, giving 19.3 g of a colourless liquid, which consists of 85% of product, $(C_2F_5)_3P=O$, and 15% of tris(pentafluoroethyl)difluorophosphorane. The two compounds can be separated by distillation, and the starting material obtained can be re-used.

Example 4

Tris(pentafluoroethyl)phosphine oxide, $(C_2F_5)_3P=O$

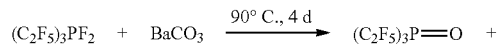

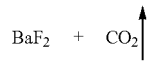

5.07 g (25.7 mmol) of barium carbonate 10.48 g (24.6 mmol) are initially introduced in a glass apparatus, and tris(pentafluoroethyl)difluorophosphorane, $(C_2F_5)_3PF_2$, are added at room temperature and with stirring using a magnetic stirrer. The reaction mixture is heated at 90° C. (temperature of the oil bath) with stirring for 4 days. The liquid is subsequently condensed into a cold trap in vacuo, giving 8.58 g of a colourless liquid, which consists of 51% of product, $(C_2F_5)_3P=O$, and 49% of tris(pentafluoroethyl)difluorophosphorane. The two compounds can be separated by distillation, and the starting material obtained can be re-used.

Example 5

Tris(nonafluorobutyl)phosphine oxide, $(C_4F_9)_3P=O$

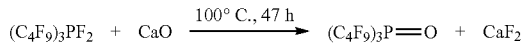

2.0 g (35.2 mmol) of finely ground calcium oxide powder (CaO) are initially introduced in a glass apparatus, and 21.2 g (29.2 mmol) of tris(nonafluorobutyl)difluorophosphorane, $(C_4F_9)_3PF_2$, are added at room temperature and with stirring using a magnetic stirrer. The reaction mixture is heated at 100° C. (temperature of the oil bath) with stirring for 47 hours. The product, $(C_4F_9)_3P=O$, is subsequently distilled off in vacuo (boiling point 68° C. at 5.5 mbar), giving 20.1 g of a colourless liquid. The yield of tris(nonafluorobutyl)phosphine oxide corresponds to 98%, calculated from the amount of tris(nonafluorobutyl)difluorophosphorane.

The NMR spectra were measured without solvents for pure substances.

$^{19}$F NMR (pure substance; lock: $D_2O$ film; reference substance: $CCl_3F$), δ, ppm: −83.8 m (9F, $3CF_3$), −114.2 d,m (6F, $3CF_2$), −120.5 m (6F, $3CF_2$), −128.2 m (6F, $3CF_2$), $^2J_{P,F}$=85 Hz.

$^{31}$P NMR (pure substance; lock: $D_2O$ film; reference substance: 85% $H_3PO_4$), δ, ppm: 22.7 sept, $^2J_{P,F}$=85 Hz.

The invention claimed is:

1. A process for the preparation of a compound of formula (I)

$(C_xF_{2x+1})_3P(O)$          (I), where x is 1, 2, 3, 4, 5, 6, 7, 8, 9, 10, 11 or 12,
said process comprising:
reacting a compound of formula (II)

$(C_xF_{2x-1})_3PF_2$          (II), where x has one of the meanings indicated above,
with an alkaline-earth metal oxide, an alkaline-earth metal carbonate, zinc oxide, copper(I) oxide, copper(II) oxide, silver oxide, mercury(II) oxide, cadmium oxide or cadmium carbonate.

2. The process according to claim 1, said compound of formula (II) is a compound in which x is 2, 3, 4, 5 or 6.

3. The process according to claim 1, wherein said compound of formula (II) is reacted with an alkaline-earth metal oxide or an alkaline-earth metal carbonate.

4. The process according to claim 3, wherein said compound of formula (II) is reacted with CaO, $CaCO_3$, MgO or $BaCO_3$.

5. The process according to claim 1, wherein the reaction takes place at a temperature between 15° C. and 200° C.

6. The process according to claim 4, wherein said compound of formula (II) is reacted with CaO.

7. The process according to claim 1, wherein said compound of formula (I) is a compound in which x is 2, 4 or 6.

8. The process according to claim 1, wherein said compound of formula (I) is tris(pentafluoroethyl)phosphine oxide or tris(nonafluorobutyl)phosphine oxide.

9. The process according to claim 1, wherein said compound of formula (II) is tris(pentafluoroethyl)difluorophosphorane, tris(heptafluoropropyl)difluorophosphorane, tris(nonafluorobutyl)difluorophosphorane, tris(undecafluoropentyl)difluorophosphorane, or tris(tridecafluorohexyl)difluorophosphorane.

10. The process according to claim 1, wherein alkaline-earth metal oxide, alkaline-earth metal carbonate, zinc oxide, copper(I) oxide, copper(II) oxide, silver oxide, mercury(II) oxide, cadmium oxide or cadmium carbonate is used in equimolar amount or an up to two-fold excess.

11. The process according to claim 1, wherein said compound of formula (II) is a perfluoroalkylphosphoranes and is used in an excess up to a maximum of 10 mol % relative to the alkaline-earth metal oxide, alkaline-earth metal carbonate, zinc oxide, copper(I) oxide, copper(II) oxide, silver oxide, mercury(II) oxide, cadmium oxide or cadmium carbonate.

12. The process according to claim 5, wherein the reaction takes place at a temperature between 50° C. and 150° C.

13. The process according to claim 5, wherein the reaction takes place at a temperature between 70° C. and 130° C.

14. The process according to claim 1, wherein the reaction is carried out without solvents.

15. The process according to claim 1, wherein the reaction is carried out in the presence of a dialkyl ethers having alkyl groups of 2 to 4 C atoms.

16. The process according to claim 1, wherein said alkaline-earth metal oxide, alkaline-earth metal carbonate, zinc oxide, copper(I) oxide, copper(II) oxide, silver oxide, mercury(II) oxide, cadmium oxide or cadmium carbonate is in solid form.

17. The process according to claim 1, wherein said alkaline-earth metal oxide, alkaline-earth metal carbonate, zinc oxide, copper(I) oxide, copper(II) oxide, silver oxide, mercury(II) oxide, cadmium oxide or cadmium carbonate is in the form of a ground solid.

18. The process according to claim 1, wherein said compound of formula (II) is reacted with a metal oxide selected from alkaline-earth metal oxides, zinc oxide, copper(I) oxide, copper(II) oxide, silver oxide, mercury(II) oxide, and cadmium oxide, and said metal oxide is in the form of fine particles having a diameter of 10 nm to 0.1 mm.

* * * * *